(12) United States Patent
Andrews et al.

(10) Patent No.: US 9,980,847 B2
(45) Date of Patent: May 29, 2018

(54) TOTAL CONTACT CAST

(71) Applicant: BSN Medical, Inc., Charlotte, NC (US)

(72) Inventors: Hugh Andrews, Buchholz in der Nordheide (DE); Scott Andrew McCall, Fort Mill, SC (US)

(73) Assignee: BSN Medical, Inc., Charlotte, NC (US)

( * ) Notice: Subject to any disclaimer, the term of this patent is extended or adjusted under 35 U.S.C. 154(b) by 174 days.

(21) Appl. No.: 14/919,165

(22) Filed: Oct. 21, 2015

(65) Prior Publication Data

US 2016/0038329 A1   Feb. 11, 2016

Related U.S. Application Data

(62) Division of application No. 13/864,338, filed on Apr. 17, 2013, now Pat. No. 9,192,504.

(51) Int. Cl.
| | |
|---|---|
| *A61F 5/00* | (2006.01) |
| *A61F 5/01* | (2006.01) |
| *A61F 5/05* | (2006.01) |
| *A61F 13/04* | (2006.01) |
| *A61F 5/30* | (2006.01) |

(52) U.S. Cl.
CPC ............. *A61F 5/0195* (2013.01); *A61F 5/05* (2013.01); *A61F 5/30* (2013.01); *A61F 13/04* (2013.01); *A61F 13/043* (2013.01); *A61F 13/045* (2013.01)

(58) Field of Classification Search
USPC .................................................. 602/10, 12
See application file for complete search history.

(56) References Cited

U.S. PATENT DOCUMENTS

| | | | | |
|---|---|---|---|---|
| 2,189,053 | A * | 2/1940 | Bryant | A61F 13/045 602/10 |
| 2,582,242 | A * | 1/1952 | Eberl | A61F 13/04 106/162.8 |
| 2,853,067 | A * | 9/1958 | Puharich | A61F 13/04 602/8 |
| 3,780,728 | A * | 12/1973 | Stader | A61F 13/045 602/10 |
| 4,762,123 | A * | 8/1988 | Dedo | A61F 13/066 128/898 |
| 5,527,265 | A * | 6/1996 | McKeel | A61F 5/05841 428/71 |
| 6,575,490 | B1 * | 6/2003 | Laughlin | A63C 10/22 280/14.24 |
| 6,976,972 | B2 * | 12/2005 | Bradshaw | A61F 5/0111 128/882 |
| 6,991,613 | B2 * | 1/2006 | Sensabaugh | A61F 5/0111 602/23 |
| 2004/0215120 | A1 * | 10/2004 | Jensen | A61F 13/04 602/8 |

(Continued)

*Primary Examiner* — Kim M Lewis
(74) *Attorney, Agent, or Firm* — Shumaker, Loop & Kendrick, LLP (57) ABSTRACT

A lower leg and foot cast including foam padding, a stockinette, cast padding, one or more layers of conformable cast tape, a foam pad having a foot bed and left and right malleolar pads, and a foot and ankle positioning device configured to be positioned over the foam pad, the device including an under foot portion and left and right vertically-extending side extensions configured to be positioned covering the left and right malleolar pads of the foam pad.

12 Claims, 6 Drawing Sheets

(56) References Cited

U.S. PATENT DOCUMENTS

| | | | | |
|---|---|---|---|---|
| 2005/0043664 | A1* | 2/2005 | Reaux | A61F 13/04 602/63 |
| 2005/0131324 | A1* | 6/2005 | Bledsoe | A61F 5/0111 602/23 |
| 2005/0228324 | A1* | 10/2005 | Stanton | A61L 15/12 602/8 |
| 2006/0287623 | A1* | 12/2006 | Beck | A61F 13/043 602/3 |
| 2007/0191749 | A1* | 8/2007 | Barberio | A43B 7/08 602/23 |
| 2010/0145246 | A1* | 6/2010 | Cadena | A61F 13/045 602/27 |
| 2011/0282254 | A1* | 11/2011 | Gadlage | A61F 5/0118 602/3 |
| 2012/0035520 | A1* | 2/2012 | Ingimundarson | A61F 5/0111 602/23 |
| 2012/0265113 | A1* | 10/2012 | Crago | A61F 15/006 602/27 |
| 2013/0066246 | A1* | 3/2013 | Tipirneni | A61F 5/01 602/12 |

* cited by examiner

TOTAL CONTACT CAST

CROSS-REFERENCE TO RELATED APPLICATION

This Divisional application claims priority from U.S. application Ser. No. 13/864,338 filed Apr. 17, 2013, the contents of which are incorporated by reference herein.

TECHNICAL FIELD AND BACKGROUND OF THE INVENTION

The present invention relates to a total contact cast, particularly of the type used to treat wounds often encountered by diabetic patients. A total contact cast is designed to redistribute plantar pressures and reduce shock and shear forces that contribute to tissue breakdown and that interfere with the normal healing process of open plantar ulcers on the diabetic foot. The application of appropriate structures to reduce pressure on pedal wounds and alter a patient's gait to prevent injury or reinjury of the tissues requires the use of several types of devices and footwear during the course of healing. The healing and post-healing stages are both important in the overall treatment sequence since treatment must include not only actual healing, but treatment after healing when newly healed tissues are thin, fragile and subject to being reinjured. Ideally, a proper treatment procedure should not only heal the wound but also protect delicate, recently healed tissues from further breakdown during the wound maturation process.

Some practitioners are reluctant to use a total contact cast. Reasons may include inadequate training, a lack of confidence to administer the treatment, a wound caused or made worse when using the treatment, or poor compliance demonstrated by diabetic neuropathic patients. The practitioner must trust a patient to follow the treatment protocol. A patient who has a demonstrated history of poor judgment in managing his or her care, with the restrictions imposed by prior art total contact casts has reduced the use of total contact casts in the past.

In order for diabetic sores and wounds to heal, substantially all of the patient's weight must be removed from the sore or wound, many of which occur on the balls of the feet.

Most practitioners treating diabetic wounds use a number of alternative off-loading devices due to a perceived complexity of applying total contact casts, concern for complications reported in the literature, the cost of materials for the device, reimbursement concerns, and a fear that application of the total contact cast will take too much time. Alternative devices used by practitioners include a removable cast walker, non-removable cast walker, instant total contact cast, molded or double upright ankle foot orthosis with or without a patellar tendon-bearing addition, Charcot restraint orthopedic walkers, modified Carville healing sandal, football dressing, commercial off-loading shoes such as the half or wedge shoes or wound care shoe systems, standard post-operative shoe, and depth or custom-molded footwear.

Most practitioners choose between these devices based on their individual experience with a particular modality, clinical availability, patient preference, or insurance reimbursement. The most commonly employed device is the surgical shoe with or without internal shoe modifications despite relatively poor evidence for healing when compared to the total contact cast or the instant total contact cast.

The diabetic patient is a complicated and often frustrating entity to treat. Patience, persistence, and a commitment to the patient are required to achieve a satisfactory result. There is therefore a need for an application method and components that allow practitioners to apply an effective total contact cast without the worry of cast misapplication common to total contact kits presently on the market. An ideal resolution produces a suspended foot within a rigid external total contact limb-load cast capable of supporting even the heaviest patient. There is also a need for a total contact cast that can be applied by a single practitioner without assistance.

SUMMARY OF THE INVENTION

It is therefore an object of the present invention to provide an effective total contact cast that will efficiently utilize the benefits desired when using a total contact cast.

It is a further object of the invention to provide an effective total contact cast that improves treatment outcomes.

It is a further object of the invention to provide an effective total contact cast that makes use of some components that are already available in the marketplace.

It is a further object of the invention to provide an effective total contact cast that makes use of some components that are adjustable or adaptable to different size patients.

It is a further object of the invention to provide a method of applying materials and components in order to achieve an effective total contact cast.

These and other objects and advantages of the invention are achieved by providing a method of constructing a total contact lower leg cast, that includes the steps of wrapping a thoroughly cleaned lower leg with foam from above the malleoli to mid-calf, covering the foot and lower leg with stockinette, overlapping a predetermined part of the previously-applied foam, and covering the foot and ankle with cast padding. A cast tape is applied to the leg over the previously-applied foam, and the cast tape is allowed to harden. A foam pad and lateral and medial malleolar pads are applied to the leg section of the cast with a second roll of casting tape. A foot and ankle positioning device is applied to the leg. The foot and ankle positioning device including a foot pad and medial and lateral side extensions extending up the medial and lateral aspects of the ankle and lower leg at a right angle to the foot pad is applied. A cast tape is applied over the lower leg and foot and allowed to harden. A walking support is applied to the foot.

In accordance with another embodiment of the invention, a foot and ankle positioner for a total contact cast is provided that includes a foot bed adapted for application to the bottom of the foot from the toes to the heel. A pair of side extensions is carried by medial and lateral sides of the foot bed and adapted for extending up the medial and lateral aspects of an ankle and lower leg to which the foot and ankle positioner is applied.

BRIEF DESCRIPTION OF THE DRAWING FIGURES

The present invention is best understood when the following detailed description of the invention is read with reference to the accompanying drawings, in which.

DETAILED DESCRIPTION OF THE PREFERRED EMBODIMENT

Figure 1:
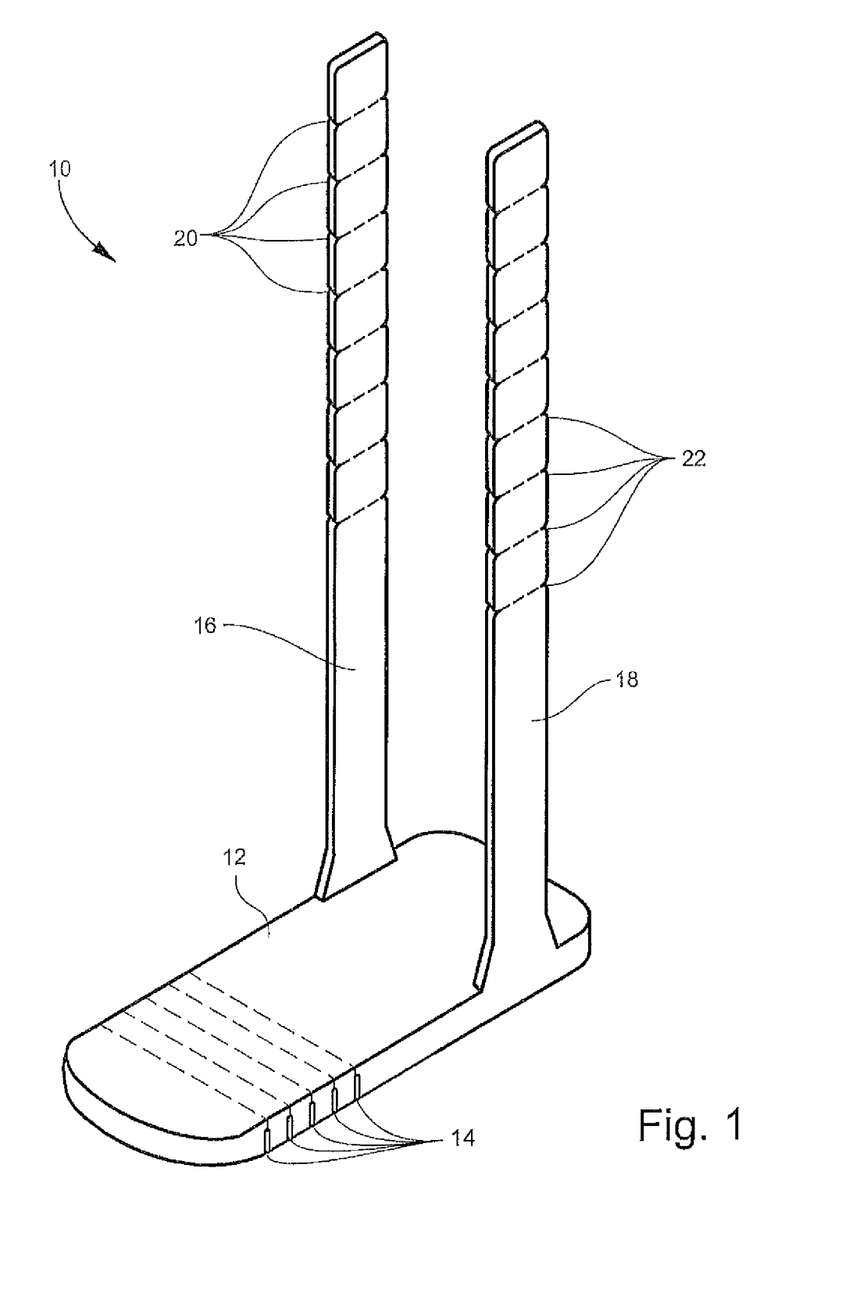
FIG. 1 is a perspective view of the foot and ankle positioning device according to one embodiment of the invention.

Referring now specifically FIG. 1 of the drawings, a foot and ankle positioning device 10 is shown. The device 10 includes a foot pad 12 preferably formed of a semi-rigid plastic. The foot pad 12 includes a series of transversely-extending scores 14 that allow the foot pad 12 to be adjusted as needed for a smaller foot by trimming off excess material at a selected one of the scores 14. The device 10 also includes a pair of vertically extending side extensions 16 and 18. The side extensions 16, 18 may optionally include respective spaced-apart scores 20, 22 that permit the side extensions 16, 18 to be shortened by trimming or snapping off as necessary to accommodate a shorter lower leg.

Figure 2:
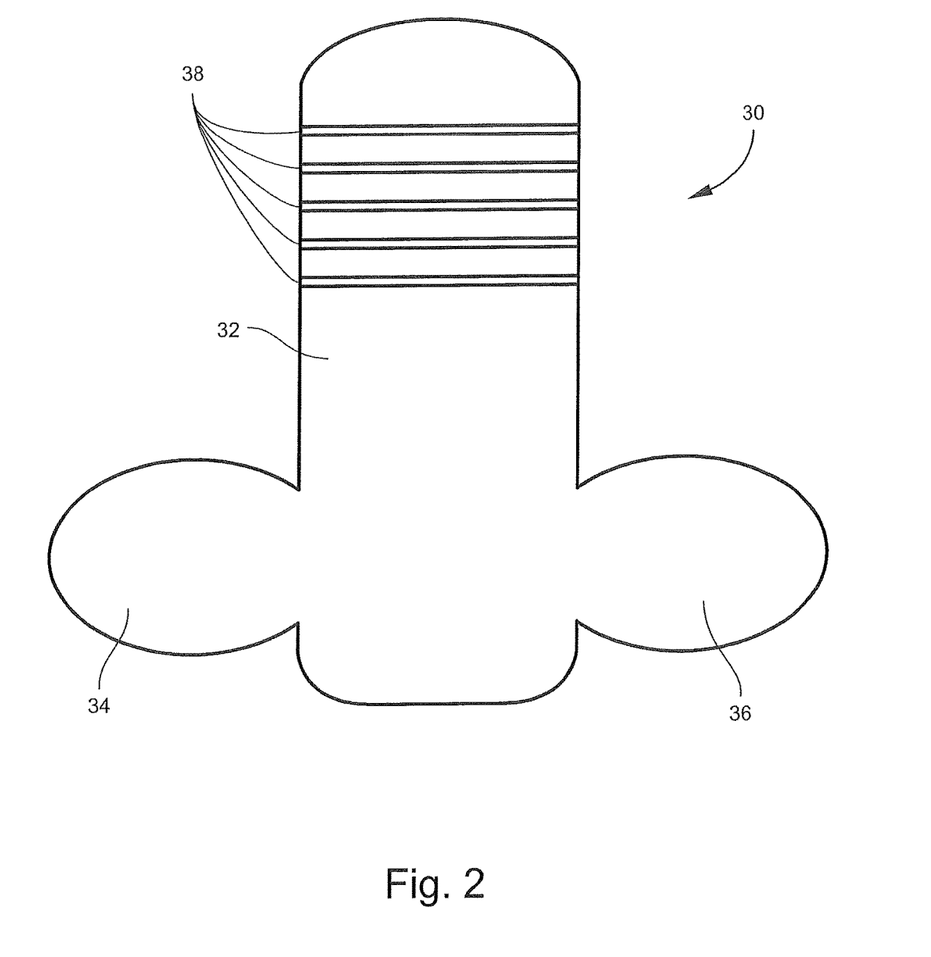
FIG. 2 is a plan view of a foam pad with medial and lateral malleolar extension pads.

FIG. 2 illustrates a foam pad 30 that includes a foot bed 32 and lateral and medial malleolar extension pads 34, 36. The foot bed 32 includes a series of transversely-extending scores 38 that permit the length of the foam pad 30 to be adjusted as necessary by trimming the excess foam material at a selected one of the scores 38. The foam that forms the pad 30 is a suitable medical grade open or closed cell foam having a preferred thickness of 2.5 cm.

Figure 3:
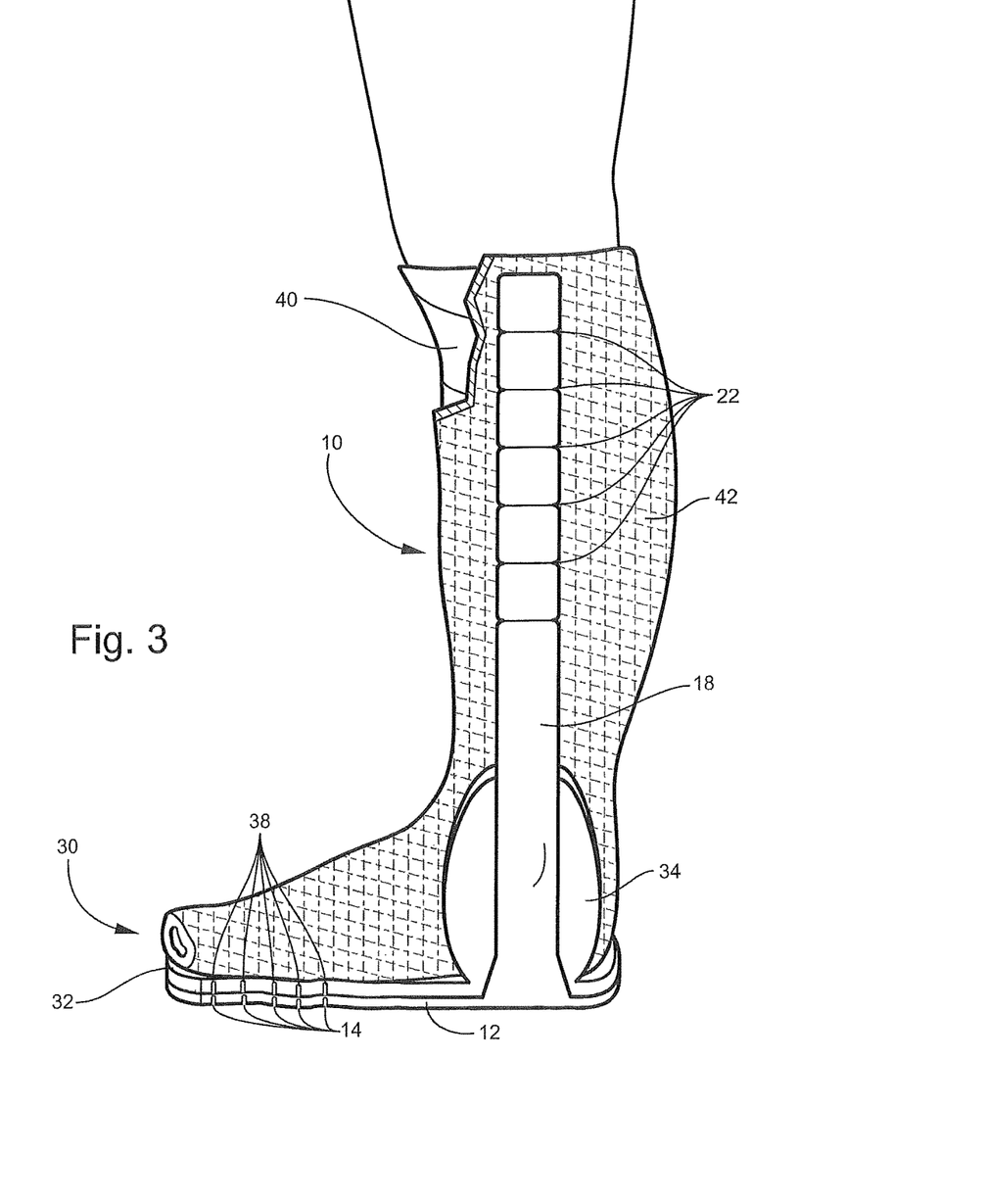
FIG. 3 is side elevation illustrating a foot and ankle positioning device and a foam pad with medial and lateral malleolar extension pads positioned on the foot and lower leg, with a portion of a stockinette covering removed to show an underlying padding.
Figure 4:
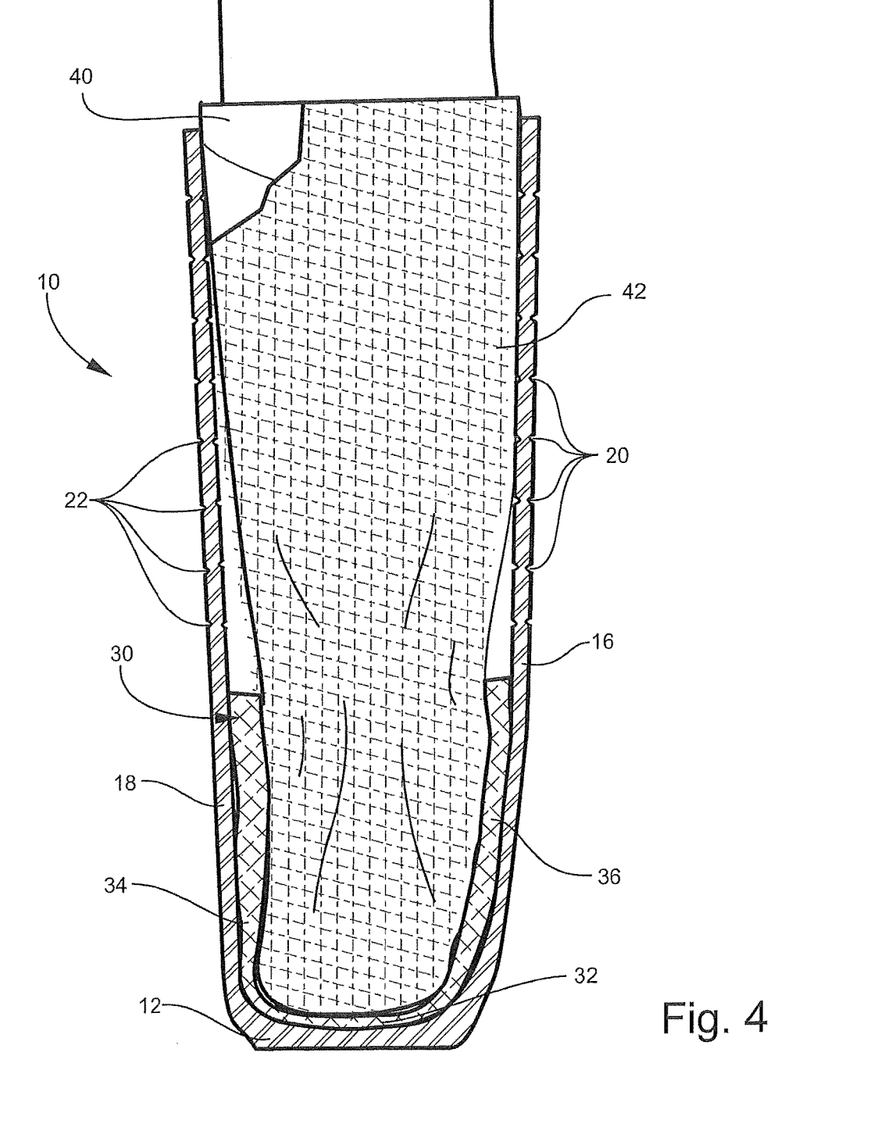
FIG. 4 is a rear elevation view showing foot and ankle positioning device and a foam pad with medial and lateral malleolar extension pads positioned on the foot and lower leg.
Figure 5:
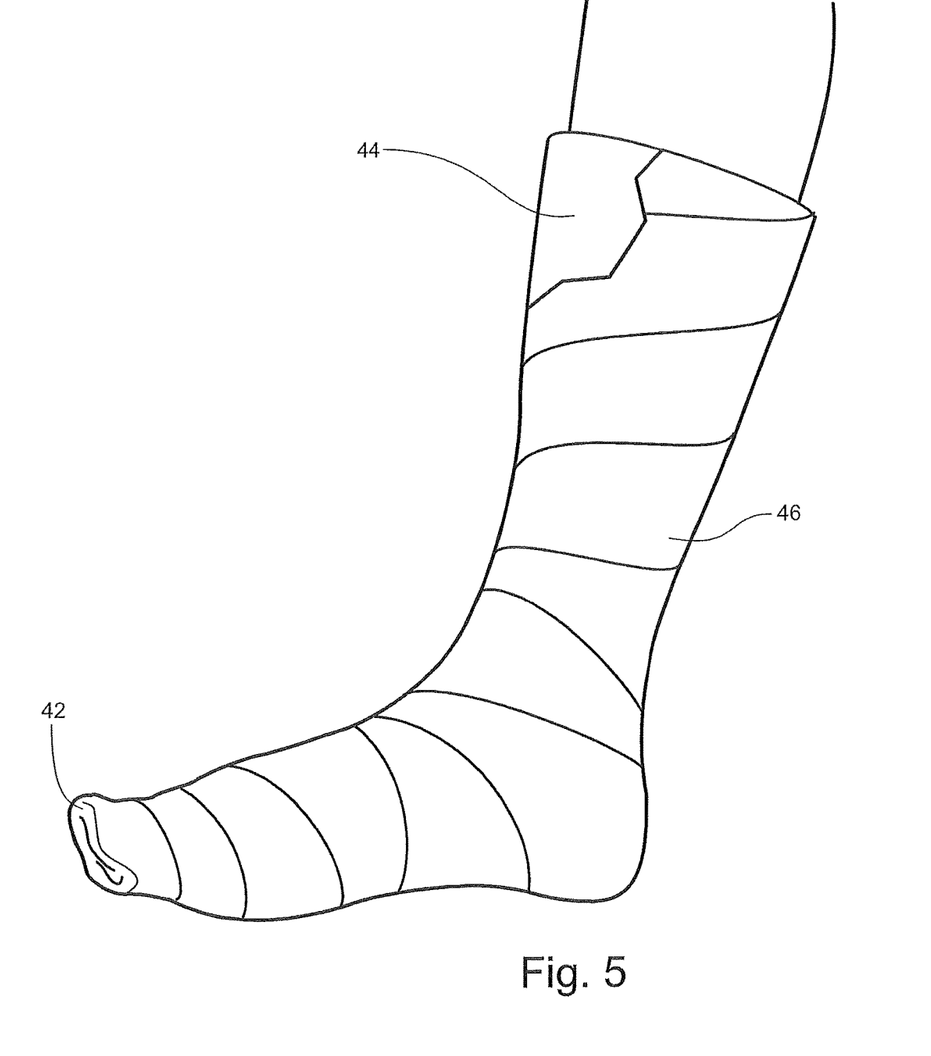
FIG. 5 is a perspective view of a lower leg and foot after wrapping with an outer bandage.

As is shown in FIG. 3, the foam pad 30 is placed under the foot and the medial and lateral malleolar extension pads 34, 36 are folded upon onto and covering the medial and lateral aspects of the ankle. This takes place after preliminary application of protective wrappings and a stockinette, as described below. The foot is then placed into the foot and ankle positioning device 10. As shown in FIG. 4, the foam pad 30 is sufficiently conformable to mold against the various irregularities and asymmetries of the ankle.

Figure 6:
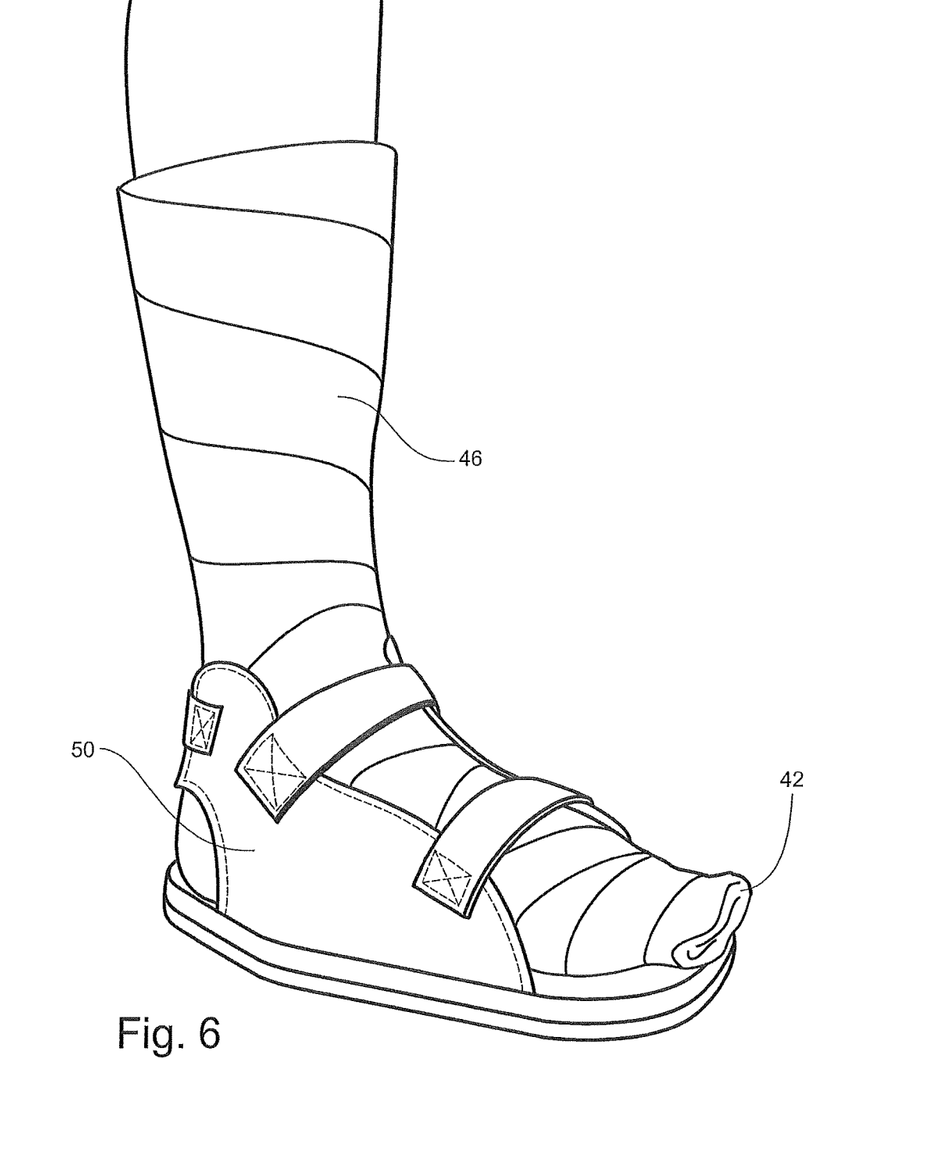
FIG. 6 is a perspective view of the completed total contact cast in a cast shoe.

The foot and ankle positioning device 10 and foam pad 30 are used in conjunction with the technique explained below. A kit, which includes the foot and ankle positioning device 10 and foam pad 30 as well as other components, includes by way of illustration:
1. One roll foam padding such as Comprifoam®: 12 cm×2.5 m×0.4 cm;
2. One 75 cm piece of stockinette;
3. 3 rolls of cast padding, which may be a synthetic or cotton padding;
4. 4 rolls of Delta Lite® Conformable cast tape, or two 4" and two 3" rolls of Delta Lite® Conformable cast tape;
5. One foot and ankle positioning device 10 and one 2.5 cm thick foam pad 30 with medial and lateral malleolar extension pads 34, 36; and
6. A cast shoe 50, as in FIG. 6, of appropriate size.

The method according to the invention proceeds by first wrapping a thoroughly cleaned lower leg and foot with a foam padding 40 such as BSN Medical padding sold under the trademark Comprifoam® from 8 cm above the malleoli to mid-calf. The foot and lower leg is then covered with stockinette 42, overlapping 4 cm. of the Comprifoam® padding 40. See FIGS. 3 and 4. The foot and ankle are then covered with cast padding in a manner similar to a standard ambulatory cast.

A conformable cast tape 44, such as BSN Medical cast tape sold under the trademark Delta-Lite® Conformable is then applied to the leg segment over the Comprifoam® previously applied, and allowed to harden.

The foam pad 30 is then positioned under the foot with the malleolar pads 34, 36 folded upwardly against the lateral and medial aspects of the ankle, attached to the leg section of the cast by application of a second roll of casting tape and adjusted to the proper size at the scores 38. The foot and ankle positioning device 10 is then applied. The structure of the foot and ankle positioning device 10 allows the practitioner to assure that the foot is held at a right angle to the leg while finishing the cast without the need of an assistant.

The application of the cast is completed by applying 2-3 rolls of additional conformable cast tape 46, which is allowed to harden. Slight weight bearing can be allowed to produce a flat base suitable for ambulation. The toe of the cast is left open.

A rocker bottom cast shoe 50 is then applied so that the patient can walk while wearing the cast.

This cast goes on as easily as a standard walking cast, eliminating fear of application mistakes. Application can be performed by one person, eliminating the need for an assistant. The resulting cast offloads the foot with a true total contact cast limb-load upper, and provides an improved protective, well-padded foot and ankle. This eliminates the chance of Achilles, malleolar or heel ulcers, or saw cuts on removal.

Alternatively, the foot and ankle positioning device 10 can be applied to the leg section of the cast after the rolls of cast padding are applied from toes to the leg and before the second and third layers are applied in order to maintain the foot and ankle in neutral position while it hardens. The foot and ankle positioning device 10 can also incorporate a rocker sole into the design to allow for a removable slipper with a non-skid base that can be worn over the cast similar to a rubber overshoe worn to protect shoes from rain. The slipper can thus be removed for sleeping in order to keep dirt out of the patient's bed.

In this manner, almost all of the patient's weight is removed from the forefoot, where most diabetic sores and wounds occur. Approximately 30 percent of the patient's weight is taken on and absorbed by the leg portion of the cast. Approximately 55 percent of the patient's weight is supported by the heel. In this regard it is important that the lower leg and foot be set and maintained at a right angle, and the structure of the foot and ankle positioning device 10 facilitates this orientation by the right angle between the foot pad 12 and the side extensions 16, 18.

A further 10 percent of the patient's body weight is supported by the midfoot area, leaving only about 5 percent of the patient's weight on the forefoot. This not only reduces direct downward pressure but also reduces shear forces that may occur as the patient pushes off on the foot during walking.

A total contact cast and total contact cast components according to the invention have been described with reference to specific embodiments and examples. Various details of the invention may be changed without departing from the scope of the invention. Furthermore, the foregoing description of the preferred embodiments of the invention and best mode for practicing the invention are provided for the purpose of illustration only and not for the purpose of limitation, the invention being defined by the claims.

What is claimed is:

1. A lower leg and foot cast system, comprising:
   a first foam pad configured to be positioned on the lower leg from above malleoli to mid-calf;
   a stockinette configured to be positioned over and overlap a portion of the first foam pad;
   cast padding configured to be positioned over the stockinette;
   a first layer of conformable cast tape configured to be positioned over the cast padding and harden upon exposure to moisture;
   a second foam pad configured to be positioned over the first layer of conformable cast tape, the second foam pad comprising a foot bed and left and right malleolar pads;
   a foot and ankle positioning device configured to be positioned over the second foam pad, the foot and ankle positioning device comprising an under foot portion configured to be positioned under and in contact with the foot bed of the second foam pad, and left and right vertically-extending side extensions configured to be positioned covering the left and right malleolar pads of the second foam pad and extend vertically upward beyond the left and right malleolar pads; and
   a second layer of conformable cast tape configured to be positioned over the foot and ankle positioning device and harden upon exposure to moisture.

2. The cast system of claim 1, further comprising a rocker bottom cast shoe configured to be worn over the second layer of conformable cast tape.

3. The cast system of claim 1, wherein the foot bed of the second foam pad comprises a plurality of spaced-apart, transversely-extending scores that permit the foot bed to be shortened in length by trimming excess foam material at a selected one of the scores.

4. The cast system of claim 1, wherein the left and right vertically-extending side extensions of the foot and ankle positioning device each comprise spaced apart scores that permit the left and right vertically-extending side extensions to be shortened in length by trimming or snapping off excess material at a selected one of the scores.

5. The cast system of claim 1, wherein the foot and ankle positioning device is made of plastic.

6. The cast system of claim 1, wherein the left and right malleolar pads of the second foam pad have a round shape.

7. A lower leg and foot cast system, comprising:
   a first foam pad comprising a foot bed for being positioned under the foot and left and right malleolar pads for being positioned against ankle bones of the lower leg;
   a foot and ankle positioning device configured to be positioned over the first foam pad, the foot and ankle positioning device comprising an under foot portion configured to be positioned under and in contact with the foot bed of the first foam pad, and left and right vertically-extending side extensions configured to be positioned covering the left and right malleolar pads of the first foam pad and extend vertically upward beyond the left and right malleolar pads;
   a second foam pad configured to be positioned on the bare lower leg from above the malleoli to mid-calf;
   a stockinette configured to be positioned over and overlap a portion of the second foam pad;
   cast padding configured to be positioned over the stockinette;
   a first layer of conformable cast tape configured to be positioned over the cast padding and harden upon exposure to moisture; and
   a second layer of conformable cast tape configured to be positioned over the foot and ankle positioning device and harden upon exposure to moisture.

8. The cast system of claim 7, further comprising a rocker bottom cast shoe configured to be worn over the second layer of conformable cast tape.

9. The cast system of claim 7, wherein the foot bed of the second foam pad comprises a plurality of spaced-apart, transversely-extending scores that permit the foot bed to be shortened in length by trimming excess foam material at a selected one of the scores.

10. The cast system of claim 7, wherein the left and right vertically-extending side extensions of the foot and ankle positioning device each comprise spaced apart scores that permit the left and right vertically-extending side extensions to be shortened in length by trimming or snapping off excess material at a selected one of the scores.

11. The cast system of claim 7, wherein the foot and ankle positioning device is made of plastic.

12. The cast system of claim 7, wherein the left and right malleolar pads of the first foam pad have a round shape.

* * * * *